(12) United States Patent
Scoones (10) Patent No.: US 9,961,896 B2
(45) Date of Patent: May 8, 2018

(54) CLEANING LIQUID

(71) Applicant: Robert Scoones, Salisbury (GB)

(72) Inventor: Robert Scoones, Salisbury (GB)

(73) Assignee: JVS PRODUCTS LIMITED, Hampshire (GB)

( * ) Notice: Subject to any disclaimer, the term of this patent is extended or adjusted under 35 U.S.C. 154(b) by 0 days. days.

(21) Appl. No.: 14/916,153

(22) PCT Filed: Aug. 29, 2014

(86) PCT No.: PCT/GB2014/052614
§ 371 (c)(1),
(2) Date: Mar. 2, 2016

(87) PCT Pub. No.: WO2015/028806
PCT Pub. Date: Mar. 5, 2015

(65) Prior Publication Data
US 2016/0212994 A1    Jul. 28, 2016

(30) Foreign Application Priority Data

Sep. 2, 2013  (GB) .................. 1315573.4

(51) Int. Cl.
| | |
|---|---|
| *A01N 33/12* | (2006.01) |
| *A01N 47/44* | (2006.01) |
| *A01N 35/08* | (2006.01) |
| *A61K 8/34* | (2006.01) |
| *A61K 8/41* | (2006.01) |
| *A61K 8/43* | (2006.01) |
| *A61K 8/02* | (2006.01) |
| *A61Q 17/00* | (2006.01) |
| *A61Q 19/10* | (2006.01) |
| *C11D 3/48* | (2006.01) |
| *C11D 1/62* | (2006.01) |
| *C11D 3/24* | (2006.01) |
| *B08B 3/08* | (2006.01) |
| *C02F 1/50* | (2006.01) |
| *C02F 1/76* | (2006.01) |
| *A61L 2/18* | (2006.01) |
| *A01N 31/02* | (2006.01) |
| *A01N 31/08* | (2006.01) |

(52) U.S. Cl.
CPC ............. *A01N 33/12* (2013.01); *A01N 31/02* (2013.01); *A01N 31/08* (2013.01); *A01N 35/08* (2013.01); *A01N 47/44* (2013.01); *A61K 8/0208* (2013.01); *A61K 8/34* (2013.01); *A61K 8/345* (2013.01); *A61K 8/347* (2013.01); *A61K 8/416* (2013.01); *A61K 8/418* (2013.01); *A61K 8/43* (2013.01); *A61L 2/18* (2013.01); *A61Q 17/005* (2013.01); *A61Q 19/10* (2013.01); *B08B 3/08* (2013.01); *C02F 1/50* (2013.01); *C02F 1/76* (2013.01); *C11D 1/62* (2013.01); *C11D 3/24* (2013.01); *C11D 3/48* (2013.01); *A61K 2800/34* (2013.01); *A61K 2800/5922* (2013.01); *C02F 2303/04* (2013.01); *C02F 2305/02* (2013.01)

(58) Field of Classification Search
CPC ........ A61K 8/0208; A61K 8/34; A61K 8/345; A61K 8/347; A61K 8/416; A61K 8/418; A61K 8/43; A61K 2800/34; A61K 2800/5922; A61L 2/18; A61Q 17/005; A61Q 19/10; B08B 3/08; C02F 1/50; C02F 1/76; C11D 1/62; C11D 3/24; C11D 3/48; A01N 33/12; A01N 31/02; A01N 31/08; A01N 35/08; A01N 47/44
See application file for complete search history.

(56) References Cited

U.S. PATENT DOCUMENTS

| | | | | |
|---|---|---|---|---|
| 6,262,003 B1 * | 7/2001 | Leonard | ............ | C11D 17/0021 510/238 |
| 6,436,885 B2 * | 8/2002 | Biedermann | ........ | A61K 8/0208 510/131 |
| 2001/0016589 A1 * | 8/2001 | Modak | .................... | A01N 47/44 514/310 |
| 2009/0269380 A1 | 10/2009 | Baker, Jr. et al. | | |
| 2010/0279906 A1 * | 11/2010 | Schwarz | ................ | A23L 3/3463 510/111 |
| 2012/0157540 A1 | 6/2012 | McGeechan et al. | | |

FOREIGN PATENT DOCUMENTS

| | | |
|---|---|---|
| EP | 0457656 A1 | 11/1991 |
| GB | 2336312 A | 10/1999 |
| GB | 2457586 A | 8/2009 |
| GB | 2457322 A | 12/2009 |
| GB | 2464399 A | 4/2010 |
| JP | 11-240808 A | 9/1999 |
| JP | 2001-354505 A | 12/2001 |
| JP | 2003-206205 A | 7/2003 |
| WO | WO 02/062142 A1 | 8/2002 |
| WO | WO 2006/116778 A2 | 11/2006 |
| WO | WO 209/010749 A2 | 1/2009 |

(Continued)

OTHER PUBLICATIONS

Dupont et al (1995) The Infectivity of Cryptosporidium parvum in Healthy Volunteers, The New England Journal of Medicine, 332(13) pp. 855-859.

(Continued)

*Primary Examiner* — Blessing M Fubara
(74) *Attorney, Agent, or Firm* — Arent Fox LLP (57) ABSTRACT

The present invention relates to a cleaning liquid, in particular a cleaning liquid for cleaning surfaces and/or for sanitizing water.

3 Claims, 5 Drawing Sheets

(56) References Cited

FOREIGN PATENT DOCUMENTS

| WO | WO 2010/097639 A2 | 9/2010 |
| WO | WO 2011/112478 A1 | 9/2011 |
| WO | WO 2012/080918 A2 | 6/2012 |
| WO | WO 2013/061082 A1 | 5/2013 |
| WO | WO 2013/098547 A1 | 7/2013 |

OTHER PUBLICATIONS

BS EN 13704: 2002 Chemical disinfectants. Quantitative suspension test for the evaluation of sporicidal activity of chemical disinfectants used in food, industrial, domestic and institutional areas. Test method and requirements (phase 2, step 1), pp. 1-2.

BS EN 13727:2012 + A2:2015;Chemical disinfectants and antiseptics. Quantitative suspension test for the evaluation of bactericidal activity in the medical area. Test method and requirements (phase 2, step 1), pp. 1-2.

BS EN 1500:2013 Chemical disinfectants and antiseptics. Hygienic handrub. Test method and requirements (phase 2/step 2), pp. 1-2.

BS EN 1650: 2008+A1:2013 Chemical disinfectants and antiseptics. Quantitative suspension test for the evaluation of fungicidal or yeasticidal activity of chemical disinfectants and antiseptics used in food, industrial, domestic and institutional areas. Test method and requirements (phase 2, step 1), pp. 1-2.

BS EN1276: 2009 Chemical disinfectants and antiseptics . Quantitative suspension test for the evaluation of bactericidal activity of chemical disinfectants and antiseptics used in food, industrial, domestic and institutional areas. Test method and requirements (phase 2, step 1), pp. 1-2.

BS EN13623: 2010 Chemical disinfectants and antiseptics. Quantitative suspension test for the evaluation of bactericidal activity against Legionella of chemical disinfectants for aqueous systems. Test method and requirements (phase 2, step 1), pp. 1-2.

Regulation (EC) 1907/2006 (REACH) see http://eur-lex.europa.eu/legal-content/EN/TXt/?url=CELEX%3A02006R1907-20140410, pp. 1-520.

Unhoch M J et al., "Recreational Water Treatment Biocides" In Paulus W (editor), Directory of Microbicides for the Protection of Materials, Kluwer Academic Publishers, 2005, Section 5.3, pp. 141-155.

Widmer G et al. (2002) Molecular mechanisms of chemical inactivation of Cryptosporidium oocysts and Giardia cysts, AwwaRF and AWWA Research Foundation ISBN 1583212450.

International Search Report issued in International Patent Application No. PCT/GB2014/052614 dated Nov. 24, 2014.

* cited by examiner

CLEANING LIQUID

CROSS REFERENCE TO RELATED APPLICATION

This application is a 35 U.S.C. 371 National Phase of PCT Application No. PCT/GB2014/052614 FILED Aug. 29, 2014, which claims priority to British Patent Application No. 1315573.4 filed Sep. 2, 2013, the disclosure of these prior applications are hereby incorporated in their entirety by reference.

FIELD OF THE INVENTION

The present invention relates to a cleaning liquid. More particularly, the present invention relates to a cleaning liquid for sanitising surfaces and sanitising water supplies. The present invention also relates to a method of forming a cleaning liquid.

BACKGROUND OF THE INVENTION

Surfaces often come into contact with, provide an environment for and provide a breeding ground for, potentially harmful pathogens. Non-limiting examples of surfaces include floors, table tops, and kitchen side boards, having any angle relative to ground level and of any shape, i.e. reference to surfaces is not limited to flat surfaces. A potentially harmful pathogen is any organism which can cause disease. Non-limiting examples of potentially harmful pathogens include bacteria, fungi, viruses, allergens, moulds and yeasts.

It is common to clean surfaces with agents which act to mitigate and/or destroy potentially harmful pathogens. The cleaning of surfaces in this way is beneficial to human and animal health, so as to prevent the spread of disease and mitigate the chances of a subject or subjects contracting a disease by coming into contact with potentially harmful pathogens.

One environment where it is particularly beneficial to clean surfaces with agents which act to mitigate and/or destroy potentially harmful pathogens is a veterinary environment, e.g. in a veterinary operating theatre.

Another environment where it is particularly beneficial to clean surfaces with agents which act to mitigate and/or destroy potentially harmful pathogens is a hospital environment, e.g. in a hospital operating theatre.

Another environment where it is particularly beneficial to clean surfaces with agents which act to mitigate and/or destroy potentially harmful pathogens is in a public amenity, e.g. the floor around a swimming pool.

There are many other environments where it is particularly beneficial to clean surfaces with agents which act to mitigate and/or destroy potentially harmful pathogens including, but not limited to, general household cleaning, hospitality venues, hotels, nursing homes, cruise ships and industrial food processing equipment.

Surfaces in veterinary operating theatres, hospitals, public amenities and other areas where people or animals could come into contact with harmful pathogens, should be cleaned regularly to prevent the build up of potentially harmful pathogens. Cleaning liquids used to clean surfaces include bleach solutions, solutions of washing up liquid, alcohol based disinfectants and general disinfectant liquid. One non-limiting example of a disinfectant liquid is Dettol™, as currently sold in the UK by Reckitt Benckiser™.

In using cleaning liquids, cleaning liquid is often transferred from storage, e.g. a bucket or a bowl, or other container, to a surface potentially contaminated with one or more pathogens.

In cleaning surfaces and/or water supplies, in particular in cleaning surfaces in hospitals, it is preferable for the anti-pathogen agent to be active in the presence of organic matter for a number of minutes, for example, up to 1, 2, 3, 4, 5, 10, 15, 20, 25, 30, 35, 40, 45, 50, 55, 60, 70, 80 and 90 minutes, 2, 3, 4, 5, 6, 7, 8, 9, 10, 11, 12, 13, 14, 15, 16, 17, 18, 19, 20, 21, 22, 23 and 24 hours, and all other times in between. It is particularly preferable for the anti-pathogen agent to be active for at least 60 minutes up to 24 hours in a hospital environment so that a cleaner may continue to use a cleaning solution containing a cleaning liquid for a suitable amount of time, without having to repeatedly replenish the cleaning solution, for example because the activity of the anti-pathogen agent has decreased.

Known floor cleaning formulations include bleach solutions, these are effective at destroying pathogens on surfaces. However, bleach can be harmful to humans and animals in its own right. Solutions of washing up liquid have relatively weak anti-pathogen activity. Alcohol based disinfectants are used, but the alcohol, which has anti-pathogen activity, is relatively volatile so it evaporates off and has a relatively short anti-pathogen activity time.

It is preferable for cleaning liquids, specifically those used in a hospital environment, to have a relatively long (around 1 hour) anti-pathogen activity time so that after, for example, a floor has been mopped the anti-pathogen activity continues for long enough that pathogens do not have a chance to settle and/or grow in between cleaning cycles. Disinfectant liquid, e.g. Dettol™, is effective in its anti-pathogen activity, but many pathogens build up resistance to long-used disinfectants.

Cleaning liquids are also used in water supplies, e.g. in swimming pools, hot tubs (for example Jaccuzzis™) and spas where persons come into contact with communal water. Water supplies in swimming pools are often treated by chlorination. Water supplies in hot tubs are often treated by ozonation and/or by the introduction of halogens, e.g. bromine, into the water supply.

In the case of a particular pathogen, namely, *Cryptosporidium parvum*, contamination of swimming pool and recreational waters is a serious problem. Once the waters become contaminated, it is easy for the organism to be transmitted into humans and infection can occur from as little as 132 oocysts (DuPont et al., (1995), The Infectivity of *Cryptosporidium parvum* in Healthy Volunteers, 332(13): 855-859). The current treatment of these waters with chlorine is ineffective to eliminate this organism, as previous studies have shown that treatment with 4 ppm chlorine at pH 7 for 25 hours resulted in no decrease in cell viability as seen by the DAPI/PI assay, and only a 40% reduction in cell viability when using the excystation assay (Widmer, (2002), Molecular mechanisms of chemical inactivation of *Cryptosporidium* oocysts and *Giardia* cysts, AWWA Research Foundation).

There is a need for a new cleaning liquid which can be applied to surfaces, and used in water treatment, which is effective in mitigating pathogen counts and has limited, or no, harmful side effects on humans and animals.

SUMMARY OF THE INVENTION

According to a first aspect of the present invention, there is provided a cleaning liquid for inhibiting pathogens, the cleaning liquid comprising:

benzalkonium chloride,
didecyl dimethyl ammonium chloride,
poly hexamethylene biguanide hydrochloride,
bronopol, and
p-chloro-m-cresol.

Preferably, further comprising an alkylene glycol.

Further preferably, wherein the alkylene glycol is ethylene glycol, propylene glycol, diethylene glycol, block copolymers of ethyleneoxide and propyleneoxide, any other alkylene glycol formed from combining alkylene oxides and/or any combination of alkylene glycols.

Advantageously, wherein the alkylene glycol comprises or consists of ethylene glycol.

Preferably, wherein the cleaning liquid does not include one or more siloxanes.

Further preferably, wherein the cleaning liquid comprises 0.5-2.5 weight % alkylene glycol.

Advantageously, wherein the cleaning liquid comprises 0.01-0.1 weight % p-chloro-m-cresol.

Preferably, wherein the cleaning liquid comprises, in weight %:
0.5-10 benzalkonium chloride,
0.5-10 didecyl dimethyl ammonium chloride,
0.5-10 poly hexamethylene biguanide hydrochloride,
0.3-5 bronopol, and
0.01-0.1 p-chloro-m-cresol.

Further preferably, wherein the cleaning liquid comprises, or consists of:
benzalkonium chloride;
didecyl dimethyl ammonium chloride;
poly hexamethylene biguanide hydrochloride;
bronopol;
p-chloro-m-cresol;
ethanol; and,
ethylene glycol.

Advantageously, wherein the cleaning liquid comprises, or consists of, in weight %:
0.5-10 benzalkonium chloride;
0.5-10 didecyl dimethyl ammonium chloride;
0.5-10 poly hexamethylene biguanide hydrochloride;
0.3-5 bronopol;
0.01-0.1 p-chloro-m-cresol;
3-10 ethanol; and,
0.5-2.5 ethylene glycol;
and/or any intermediate value of each range for each component; the balance being water.

Preferably, wherein the cleaning liquid comprises, or consists of, in weight %:
3 benzalkonium chloride;
3 didecyl dimethyl ammonium chloride;
3.3 poly hexamethylene biguanide hydrochloride;
0.9 bronopol;
0.04 p-chloro-m-cresol;
4.9 ethanol; and,
1.0 ethylene glycol;
the balance being water.

According to another aspect of the present invention, there is provided an aqueous mixture comprising: water and a cleaning liquid according to any one of the above.

Preferably, wherein the water is tap water, potable water, distilled water, dirty water, water containing soil, water containing effluent, water containing pathogens, water containing waste, waste water and/or brackish water.

Further preferably, wherein the composition has a ratio of water by volume to cleaning liquid of from 99% water to 1% cleaning liquid to 1% water to 99% cleaning liquid, or any intermediate value.

Advantageously, wherein the composition has a ratio of water by volume to cleaning liquid of 99%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1.5%, 1%, 0.9%, 0.8%, 0.7%, 0.6%, 0.5%, 0.4%, 0.3%, 0.2%, 0.1% or 0.05% water to cleaning liquid.

Preferably, wherein the composition has a ratio of water by volume to cleaning liquid of from 99% water to 1% cleaning liquid.

According to another aspect of the present invention, there is provided a method of cleaning a surface, comprising:
providing a cleaning liquid or an aqueous mixture according to any one of the above; and,
applying the mixture to a surface.

According to another aspect of the present invention, there is provided a method of sanitising water, comprising:
providing a cleaning liquid or an aqueous mixture according to any one of the above; and,
contacting the cleaning liquid or aqueous mixture with water to be sanitised.

According to another aspect of the present invention, there is provided a method of preparing a cleaning liquid according to any one of the above, comprising:
providing the components according to any one of the above; and,
mixing the ingredients in a mixer.

According to another aspect of the present invention, there is provided a wipe for application to skin, the wipe comprising a cleaning liquid or an aqueous mixture according to any one of the above.

According to another aspect of the present invention, there is provided the use of a cleaning liquid or an aqueous mixture of any one of the above, in any one of:
cleaning a surface;
sanitising a water supply; or
disinfecting an area of skin.

Preferably, the use in sanitising a water supply, wherein the cleaning liquid or aqueous mixture of any one of the above is used as a supplement, or in addition to, chlorine water treatment.

DETAILED DESCRIPTION

Composition A

Some of the components of cleaning liquids of the present invention, together with their sources, are set out below.

Composition A, also referred to as SQ53 in this specification (sometimes referred to as JVS 90 or JVS Formula 90 by the inventor, but not in this specification), is a non-limiting example of a composition according to the present invention:

| Marketed name | Generic name | CAS number | Composition A Amount (weight %) in neat | Amount (weight %) in 1:19 v/v |
|---|---|---|---|---|
| Acticide BAC50M | Benzalkonium chloride | 63449-41-2 | 3 | 0.15 |
| Acticide DDQ50 | Didecyl Dimethyl Ammonium Chloride | 7173-51-5 | 3 | 0.15 |
| Acticide PHB20 | Poly Hexamethylene Biguanide Hydrochloride | 27083-27-8 | 3.3 | 0.165 |
| Acticide L | Bronopol | 52-51-7 | 0.9 | 0.045 |
| Acticide PCMC | P-chloro-m-cresol | 59-50-7 | 0.04 | 0.002 |
| | Ethanol | 64-17-5 | 4.9 | 0.245 |
| | Ethylene glycol | 107-21-1 | 1.0 | 0.05 |
| | Aqua | | 83.86 | 99.193 |

Composition A is a composition according to a preferred embodiment of the present invention. The names of the ingredients are listed, along with their CAS (Chemical Abstract Service) number. The CAS number has been given because the CAS registry is a standard reference for persons looking to classify chemical compounds which are known in the scientific literature. In all of the compositions, the amount of each ingredient is provided in weight % (also referred to in this specification as wt % or % w/w). The column "amount . . . in neat" shows the neat composition. The column "amount . . . in 1:19 v/v" shows the amount of each component in a 1:19 v/v neat composition-water solution. The indication "v/v" indicates the ratio is by volume.

Components of Composition A

Benzalkonium chloride is a mixture of alkylbenzyldimethylammonium chlorides of various even-numbered alkyl chain lengths. Benzalkonium chloride may act as inter alia a biocide, a cationic surfactant and a phase transfer agent. A non-limiting example of a batch size for composition A is 10 kg.

Didecyl Dimethyl Ammonium Chloride is a compound which acts as inter alia an antiseptic and/or a disinfectant, i.e. a biocide.

Poly Hexamethylene Biguanide Hydrochloride is a polymer which acts as inter alia a disinfectant and/or an antiseptic, i.e. a biocide.

Bronopol is a compound which acts as inter alia an antimicrobial, i.e. a biocide. Bronopol is commonly used as a preservative in consumer products, e.g. in cosmetics.

P-chloro-m-cresol (4-chloro-3-methylphenol) is a compound which acts as inter alia an antiseptic and a preservative, i.e. a biocide. P-chloro-m-cresol is often used in handwash.

Ethanol is a colourless liquid often used as a solvent.

Ethylene glycol is a compound commonly used in antifreeze and as a precursor to some polymers. In other embodiments, ethylene glycol may be substituted, in whole or in part, with other alkylene glycols, for example: propylene glycol, diethylene glycol, block copolymers of ethyleneoxide and propyleneoxide (e.g. different types of Pluronic™ as sold by BASF™), any other alkylene glycol formed from combining alkylene oxides and/or any combination of alkylene glycols.

Manufacturing Protocol for Composition A

The following is a protocol for forming a cleaning liquid according to composition A shown above. The amounts of each ingredient used at each step are shown above, i.e. they are not specified in the method below.

In one exemplary embodiment, all of the ingredients of composition A are mixed in any order, in the amounts specified in the tables, to result in a formulation according to the present invention.

In another exemplary embodiment, composition A is prepared as follows:
 i. Select a clean manufacturing vessel, e.g. a stainless steel mixing vessel with a propeller shaft.
 ii. Ensure any inlets or outlets from the manufacturing vessel are clean.
 iii. Measure out all raw materials, as required for the composition.
 iv. Optionally, add water for the desired final dilution.
 v. Introduce the following components, preferably in order: (1) Acticide PCMC; (2) Acticide L (3) Acticide BAC 50; (4) Acticide DDQ 50; (5) Acticide PHB20, mixing the components either continuously or after each introduction.
 vi. Separately add in ethanol, followed by ethylene glycol, mixing continuously at 25° C. and 100 kPa, and until all components are dissolved.
 vii. Optionally, add additional water to dilute the mixture to a desired degree.

The composition is optionally filtered with a 25 micron filter.

Ranges for each of the ingredients in composition A are provided in the table below. All compositions falling within these boundaries are expected to have the same effects. The ranges are provided to show the ranges which have been tested. The ranges each include each intermediate value, e.g. 10-20 includes 10, 11, 12, 13, 14, 15, 16, 17, 18, 19 and 20, and each further intermediate value.

Composition A Ranges (Example):

| Marketed name | Generic name | CAS number | Composition A Amount (weight %) in neat | Ranges for composition A Amount (weight %) in neat |
|---|---|---|---|---|
| Acticide BAC50M | Benzalkonium chloride | 63449-41-2 | 3 | 0.5-10 |
| Acticide DDQ50 | Didecyl Dimethyl Ammonium Chloride | 7173-51-5 | 3 | 0.5-10 |
| Acticide PHB20 | Poly Hexamethylene Biguanide Hydrochloride | 27083-27-8 | 3.3 | 0.5-10 |
| Acticide L | Bronopol | 52-51-7 | 0.9 | 0.3-5 |
| Acticide PCMC | P-chloro-m-cresol | 59-50-7 | 0.04 | 0.01-0.1 |
| | Ethanol | 64-17-5 | 4.9 | 3-10 |
| | Ethylene glycol | 107-21-1 | 1.0 | 0.5-2.5 |
| | Aqua | | 83.86 | 52.40-94.69 |

Composition A, according to the present invention, is in compliance with Regulation (EC) 1907/2006 (REACh). In other words, the ingredients comply with the relevant EC law on safety in chemicals used in domestic environments.

In an alternative embodiment, ethylene glycol can be replaced by a different alkylene glycol, e.g. mono propylene glycol. Other non-limiting examples of alkylene glycols include, but are not limited to, diethylene glycol, block copolymers of ethyleneoxide and propyleneoxide (e.g. different types of Pluronic™ as sold by BASF™), any other alkylene glycol formed from combining alkylene oxides and/or any combination of alkylene glycols.

In use, the compositions of the present invention are mixed with water. Preferable mixing ratios with water for exemplary neat composition A is, in percentage terms (where 1% means 99 parts water to 1 part exemplary composition) 100%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1.5%, 1%, 0.9%, 0.8%, 0.7%, 0.6%, 0.5%, 0.4%, 0.3%, 0.2%, 0.1% and 0.05%. An optional mixing ratio is 1%. Preferred embodiments include mixing neat composition with from 15 to 25 parts water (or any intermediate value) to one part neat composition A, by volume. In a particularly preferred embodiment, the neat composition is mixed with water in a one part neat composition to 19 parts water ratio (1:19 v/v), i.e. as shown in the right hand column of the table highlighting neat composition A. In another particularly preferred embodiment, the neat composition is mixed with water in a one part neat composition to 20 parts water ratio (1:20 v/v). In another particularly preferred embodiment, the neat composition is mixed with water in a one part neat composition to 60 parts water ratio (1:60 v/v).

In use, the cleaning compositions of the present invention are applied to a surface by an applicator, for example, a mop, a sponge, a cloth, a towel or a glove. In use, the cleaning compositions of the present invention are stored in a receptacle, for example, a bucket, for application by an applicator. In a particularly preferred embodiment, the cleaning compositions of the present invention are stored in a bowl and applied to a surface by a cloth.

In an alternative use, the cleaning compositions of the present invention are introduced into a water supply, e.g. a water supply for used in or to be introduced into a swimming pool. The water supply is contacted with the cleaning composition and then re-introduced into the swimming pool.

In an alternative use, the cleaning compositions of the present invention are introduced onto the skin of a user, e.g. by way of a wipe or by spraying.

Sanitising Surfaces Tests
1. A Variety of Pathogens

A number of tests were carried out on composition A by D C Watson at Abbott Analytical, in New Ferry, UK, under a non-disclosure agreement. These tests were performed under different European standards, using 1:20 v/v dilution of the 'neat' version of composition A with water. These European standards are referred to as EN XX, where XX is the number assigned to the standard test by the relevant European Standardisation Organisation. The conclusions of Abbott Analytical were as follows:

Composition A, when diluted to 1:20 v/v, passes the requirements of EN 1276 for bactericidal activity (*Pseudomonas aeruginosa* (NCI MB 10421), *Escherichia coli* (NCTC 10418), *Staphylococcus aureus* (NCTC 10788), *Enterococcus hirae* (NCIMB 8192)) in 5 minutes at 20° C. under dirty conditions against all of the reference organisms detailed.

Composition A, when diluted to 1:20 v/v, passes the requirements of EN 1276 for bactericidal activity (*Listeria monocytogenes* (NCTF 11994), *Salmonella typhimurium* (NCTC 74), Methicillin-resistant *Staphylococcus aureus* (NCTC 12493)) in 5 minutes at 20° C. under dirty conditions against all of the reference organisms detailed.

Composition A, when diluted to 1:20 v/v, passes the requirements of EN 13623 for bactericidal activity (*Legionella pneumophila* (NCTC 12821)) in 60 minutes at 30° C. against *Legionella pneumophila*.

Composition A, when diluted to 1:20 v/v, passes the requirements of EN 1276 for bactericidal activity (*Streptococcus dysgalactiae* (NCIMB 702023), *Streptococcus uberis* (NCIMB 2038), *Streptococcus suis* (NCTC 10234), *Streptococcus equi* (NCTC 7912)) in 5 minutes at 20° C. under dirty conditions against all of the reference organisms detailed.

Composition A, when diluted to 1:20 v/v, passes the requirements of EN 1650 for fungicidal activity (*Aspergillus fumigatus* (NCPF 7102)) in 15 minutes at 20° C. under dirty conditions against the reference organism detailed.

Composition A, when diluted to 1:20 v/v, passes the requirements of EN 13704 for sporicidal activity (*Clostridium difficile* (NCTC 11209)) in 60 minutes at 20° C. under dirty conditions against the reference organism detailed.

Composition A, when diluted to 1:20 v/v, passes the requirements of EN 13704 for sporicidal activity (*Bacillus subtilis* (NCIMB 8054), *Bacillus cereus* (ATCC 12826)) in 60 minutes at 20° C. under dirty conditions against both of the reference organisms detailed.

Composition A, when diluted to 1:20 v/v, passes the requirements of EN 1500 for hygienic hand rubs when tested under the procedures described above. This shows the composition is suitable for mitigating the presence of pathogens on hands.

In summary, composition A was found to have anti-bacterial, anti-fungicidal and anti-sporicidal effects. Composition A was also found to be suitable for use as a hand rub.

2. Safety

Furthermore, Reading Scientific Services Ltd, Reading, UK, carried out a safety evaluation of composition A, under a non-disclosure agreement. Reading Scientific Services Ltd concluded that composition A complies with the European Cosmetic Regulations and should not cause damage to health under normal and reasonably foreseeable use.

3. Effect Against MRSA and *E. coli*

Further tests were carried out on the effectiveness of the compositions of the present invention, namely, composition A detailed above.

Tests were carried out by Dr Susanna Sherwin and Professor Bill Keevil, under a non-disclosure agreement, at the Environmental Healthcare Unit at the University of Southampton, UK. Their methods and results are set out below, with reference to the figures.

Four experimental protocols were used:

A. Culturable Cell Counts: Coating Surface with Bacteria, and then Adding Biocide Overnight cultures of MRSA (20 μl) were coated on 1 cm$^2$ stainless steel coupons, and were allowed to dry; 20 μl aliquots of 5% (v/v) composition A was added to the coupons, and incubated at room temperature for 0 hours (control) or 2 hours. After incubation, cells were removed from coupons by vortexing in PBS with glass beads, and the resulting solution was diluted and plated on nutrient agar plates. After overnight incubation at 37° C., viable cells were counted. The colonies that grew on nutrient agar plates in this time period indicate the numbers of MRSA bacteria present in the original sample that were culturable in the lab, and are termed Colony Forming Units (CFUs).

B. Culturable Cell Counts: Coating Surface with Biocide, and then Adding Bacteria Stainless steel coupons were submerged in composition A, removed and allowed to dry. Overnight cultures of MRSA (20 μl) were then added to the coupons, and the coupons were incubated at room temperature for 0 hours (control) or 2 hours. After incubation, cells were removed from coupons by vortexing in PBS with glass beads, and the resulting solution was diluted and plated on nutrient agar plates. After overnight incubation at 37° C., viable cells were counted.

C. LIVE/Dead Microscopy Staining

Experiments were conducted as mentioned above, and after incubation, LIVE/Dead fluorescent stain was added to the steel coupons, and incubated in the dark for 15 minutes. Epifluorescence microscopy was used to observe total numbers of cells (green) compared to dead cells with damaged cytoplasmic membranes (red).

D. Cell Elongation Assay Using *E. coli*

An 100 μl aliquot of an overnight *E. coli* culture (strain DH5-α) was added to either 900 μl PBS buffer, or 900 μl biocide (5% v/v). After 2 hours incubation, the cells were pelleted by centrifugation, and then resuspended in 1 ml PBS. This was then added to 9 ml 50% R2 broth. Pipemidic acid (final concentration 100 μg/ml) was added to the solution to stop live cell replication, causing live cells to become elongated. Samples were incubated for 18 hours at 22° C., before staining with SYTO9 fluorescent stain. A 1 ml aliquot of the sample was filtered through 0.2 μm polycarbonate filters, and examined using epifluorescent microscopy. Normal length (dead) cells were counted, as were elongated (live) cells.

Results:

A. And B. Culturable Cell Counts

Composition A (in 1 part 'neat' to 19 parts water concentration (1:19 v/v)) resulted in bactericidal killing after two hours of contact time. However, the order in which the bacteria and biocide were added to the steel coupons proved to be crucial to the killing effect of the composition. If stainless steel coupons were pre-coated with MRSA, and the biocides were added subsequently, a 1-2 log killing effect was seen using culture methods (Table 1 and FIG. 1). However, if a sterile coupon was coated in biocide before the MRSA was introduced to the system, no viable MRSA could be detected after 2 hours incubation with (Table 1 and FIG. 2).

TABLE 1

Numbers of viable cells cultured after overnight incubation. Culturable cells are measured as colony forming units (CFU).

| Conditions | 0 Hour Average cell number (CFU ml$^{-1}$) | 2 Hour Average cell number (CFU ml$^{-1}$) | % Survival |
|---|---|---|---|
| MRSA Only | 4.13E+06 | 3.47E+06 | 83.87 |
| Precoated MRSA plus SQ53 | 6.67E+05 | 1.97E+04 | 2.96 |
| Precoated SQ53 plus MRSA | 1.77E+06 | 0.00E+00 | 0.00 |

Figure 1:
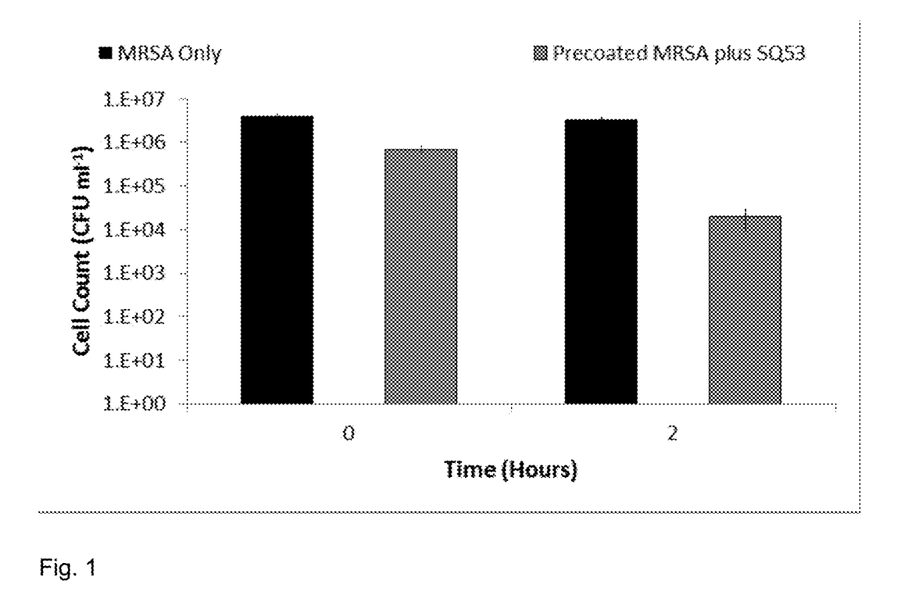
FIG. 1: Shows the average culturable bacterial count after treatment with composition A.

FIG. 1 shows the average culturable bacterial count after treatment with composition A. MRSA was pre-coated onto steel coupons, and the biocide SQ53 was added. Each bar is an average of 6 replicates, with error bars indicating standard error of the replicates.

Figure 2:
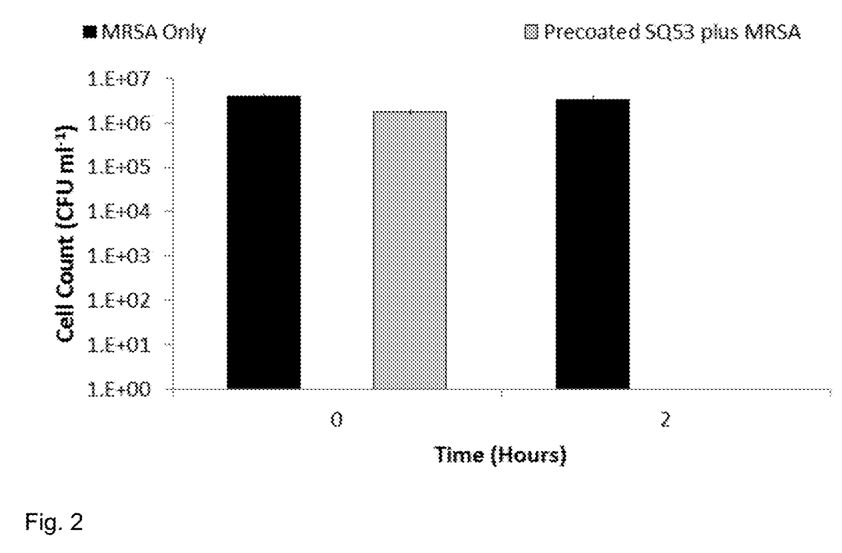
FIG. 2: Shows the averable culturable bacterial count after treatment with composition.

FIG. 2 shows the average culturable bacterial count after treatment with composition. SQ53 was pre-coated onto steel coupons, and MRSA was added. Each bar is an average of 6 replicates, with error bars indicating standard error of the replicates.

FIGS. 1 and 2 show that composition A has a strong effect against MRSA, under the test conditions specified.

C. Total Cell Count Using BacLight LIVE/Dead Viability Staining

In addition to culturing methods, treated cells were stained with fluorescent LIVE/Dead dyes so that the proportion of surviving cells could be enumerated using epifluorescence microscopy. However, whilst it was possible to collect fluorescent images of total bacterial cells using the LIVE/Dead stain, it was not possible to observe 'dead' cell fluorescent staining using the Propidium Iodide (PI) stain for compromised bacterial membranes. This may be due to the action of the composition A (i.e. SQ53), which is thought to engulf the bacterial cell, thus affecting uptake of larger molecules, such as the 'dead' stain PI.

D. Cell Elongation Study Using *E. coli*

An additional experiment was carried out in order to determine the efficacy of the biocides using microscopy. For this experiment only, a different bacterium, *E. coli* was used. After treatment with biocides, the cells were incubated with an antibiotic, Pipemidic acid. If live cells were present, they would begin to replicate, but be unable to physically separate, resulting in an elongated cell, easily visible under the microscope, whereas the dead cells remain the size of a single bacterium. An average of 50 fields of view per treatment were photographed, and using these results, the total live and dead cells per original sample can be calculated.

Figure 3:
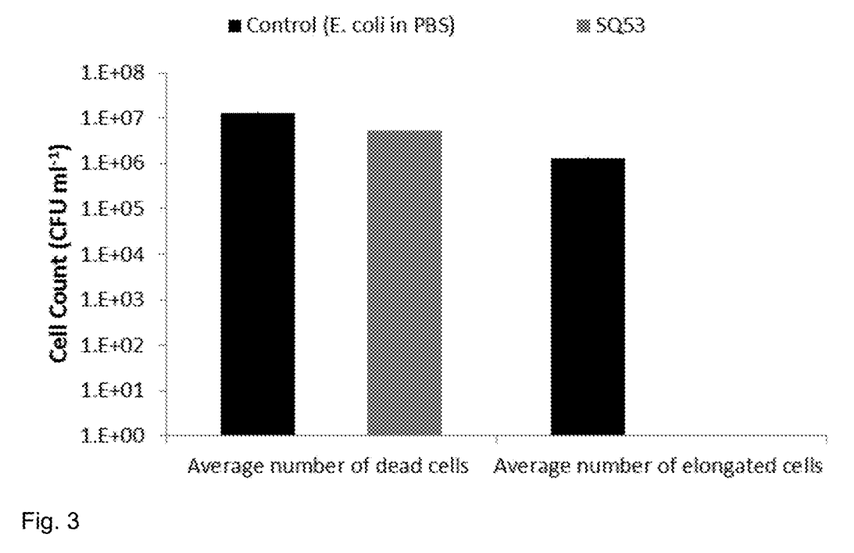
FIG. 3: Shows the total numbers of dead and live *E. coli* cells determined using the cell elongation assay.

Calculation of Numbers of Fields of View Per Filter:
One Field of View=11623.58 μm$^2$
Filter membrane diameter=21000 μm
Filter membrane are ($\pi r^2$)=346360590.1 μm$^2$
Numbers of Fields of View per filter=346360590.1/11623.58
=23963.702 fields of view Therefore the overall average total cell count per field of view was multiplied by this factor to get total cell count per filter, and thus total cell count per 1 ml sample (the data is shown in Table 2). By this method, it was possible to determine that composition A resulted in at least a 2 log kill, although in this assay, composition A seemed to result in complete killing of the *E. coli* cells (FIG. 3). However, the composition had an adverse effect on the assay. Once the cells have been treated with the composition, they become much stickier than the control cells. This meant that we were unable to completely resuspend the treated cells prior to the cell elongation assay, which resulted in decreased numbers of cells we could count (Table 2).

TABLE 2

Total numbers of dead and live *E. coli* cells determined by epifluorescence microscopy. Cells per ml were determined by calculating average cells per field of view from a total of 50 fields of view, and then calculating the number of cells per filter.

| | Average number of dead cells (cells ml$^{-1}$) | Average number of elongated cells (cells ml$^{-1}$) |
|---|---|---|
| Control (*E. coli* in PBS) | 1.31E+07 | 1.31E+06 |
| SQ53 | 5.18E+06 | 0.00E+00 |

FIG. 3 shows the total numbers of dead and live *E. coli* cells determined using the cell elongation assay. Bars indicate dead cell count, and live (elongated) cell counts as determined cell elongation assay, and error bars indicate standard error of the replicates.

The cell elongation assay, carried out on *E. coli*, was able to show that composition A, when applied to a cell culture, results in complete cell death. Composition A was found to be more effective than known cleaning liquids, whilst at the same time not including components which are harmful to human or animal health.

4. Comparative Tests

Further tests were carried out by D C Watson at Abbott Analytical, in New Ferry, UK, under a non-disclosure agreement. These tests were performed under the same European standard, using 1:20 v/v dilution of the 'neat' version of composition A.

As mentioned above, composition A passes the requirements of EN 1276 for bactericidal activity (*Pseudomonas aeruginosa* (NCI MB 10421), *Escherichia coli* (NCTC 10418), *Staphylococcus aureus* (NCTC 10788), *Enterococcus hirae* (NCIMB 8192)) in 5 minutes at 20° C. under dirty conditions against all of the reference organisms detailed.

As a comparison, solutions of Acticide BAC50M (Benzalkonium chloride), Acticide DDQ 50 (Didecyl Dimethyl Ammonium Chloride), Acticide PHB 20 (Poly Hexamethylene Biguanide Hydrochloride), Acticide L (Bronopol) and Acticide PCMC (P-chloro-m-cresol) were all tested individually under the same conditions. In these tests, the same relative amounts of ethanol, ethylene glycol and water, as in composition A, were present.

Acticide BAC50M (Benzalkonium chloride) in the same concentration as in composition A, when diluted to 1:20 v/v, does not pass the requirements of EN 1276 for bactericidal activity (*Pseudomonas aeruginosa* (NCIMB 10421), *Escherichia coli* (NCTC 10418), *Staphylococcus aureus* (NCTC 10788), *Enterococcus hirae* (NCIMB 8192)) in 5 minutes at 20° C. under dirty conditions against all of the reference organisms detailed.

Acticide DDQ50 (Didecyl Dimethyl Ammonium Chloride) in the same concentration as in composition A, when diluted to 1:20 v/v, does not pass the requirements of EN 1276 for bactericidal activity (*Pseudomonas aeruginosa* (NCIMB 10421), *Escherichia coli* (NCTC 10418), *Staphylococcus aureus* (NCTC 10788), *Enterococcus hirae* (NCIMB 8192)) in 5 minutes at 20° C. under dirty conditions against all of the reference organisms detailed.

Acticide PHB20 (Poly Hexamethylene Biguanide Hydrochloride) in the same concentration as in composition A, when diluted to 1:20 v/v, does not pass the requirements of EN 1276 for bactericidal activity (*Pseudomonas aeruginosa* (NCIMB 10421), *Escherichia coli* (NCTC 10418), *Staphylococcus aureus* (NCTC 10788), *Enterococcus hirae* (NCIMB 8192)) in 5 minutes at 20° C. under dirty conditions against all of the reference organisms detailed.

Acticide L (Bronopol) in the same concentration as in composition A, when diluted to 1:20 v/v, does not pass the requirements of EN 1276 for bactericidal activity (*Pseudomonas aeruginosa* (NCIMB 10421), *Escherichia coli* (NCTC 10418), *Staphylococcus aureus* (NCTC 10788), *Enterococcus hirae* (NCIMB 8192)) in 5 minutes at 20° C. under dirty conditions against all of the reference organisms detailed.

Acticide PCMC (P-chloro-m-cresol) in the same concentration as in composition A, when diluted to 1:20 v/v, does not pass the requirements of EN 1276 for bactericidal activity (*Pseudomonas aeruginosa* (NCIMB 10421), *Escherichia coli* (NCTC 10418), *Staphylococcus aureus* (NCTC 10788), *Enterococcus hirae* (NCIMB 8192)) in 5 minutes at 20° C. under dirty conditions against all of the reference organisms detailed.

Without wishing to be bound by theory, it is believed that the combination of Acticide BAC50M, Acticide DDQ 50, Acticide PHB 20, Acticide L and Acticide PCMC, according to compositions of the present invention, provides a synergistic effect in providing a disinfecting action. This synergistic effect is evidenced at least by the combination of these five components providing a bactericidal activity against *Pseudomonas aeruginosa* (NCIMB 10421), *Escherichia coli* (NCTC 10418), *Staphylococcus aureus* (NCTC 10788), *Enterococcus hirae* (NCIMB 8192) under an EN 1276 test; whilst under the same conditions each individual component does not pass the EN 1276 test.

Additional comparative tests were carried out by D C Watson at Abbott Analytical, in New Ferry, UK, under a non-disclosure agreement. These tests were performed under the same European standard.

Composition A passes the requirements of EN 13727: 2012+A1:2013 for bactericidal activity (*Pseudomonas aeruginosa* (NCTC 13359)) in 5 minutes at 20° C. under dirty conditions.

As an additional comparison, different solutions of mixtures of three (Table 2A) or four or five (Table 2B) of: Acticide BAC50M (Benzalkonium chloride: referred to as B in tables 2A and 2B), Acticide DDQ 50 (Didecyl Dimethyl Ammonium Chloride: referred to as A (i.e. individual component A rather than composition A above) in tables 2A and 2B), Acticide PHB 20 (Poly Hexamethylene Biguanide Hydrochloride: referred to as E is tables 2A and 2B), Acticide L (Bronopol: referred to as C in tables 2A and 2B) and Acticide PCMC (P-chloro-m-cresol: referred to as D in tables 2A and 2B); were all tested under the same conditions. In these tests, the same relative amounts of ethanol, ethylene glycol and water, as in composition A, were present. The results of Table 2A were obtained using a 1:20 v/v dilution of the 'neat' compositions. The results of Table 2B were obtained using a 1:60 v/v dilution of the 'neat' compositions.

TABLE 2A effect of mixtures under EN 13727: 2012 + A1:
2013 against *Pseudomonas aeruginosa* (NCTC 13359)

| Mix | Lg reductions against *Pseudomonas aeruginosa* |
|---|---|
| ABC | 4.04 |
| BCD | 3.96 |
| CDE | <3.86 |
| DEA | 4.47 |
| ACE | 4.50 |
| BDA | 3.97 |

TABLE 2B effect of mixtures under EN 13727: 2012 + A1:
2013 against *Pseudomonas aeruginosa* (NCTC 13359)

| Mix | Lg reductions against *Pseudomonas aeruginosa* |
|---|---|
| EABC | 4.32 |
| ABCD | 3.98 |
| CDEB | <3.88 |
| ACED | 4.24 |

TABLE 2B-continued effect of mixtures under EN 13727: 2012 + A1:
2013 against *Pseudomonas aeruginosa* (NCTC 13359)

| Mix | Lg reductions against *Pseudomonas aeruginosa* |
|---|---|
| ABDE | 4.61 |
| ABCDE | >5.24 |

Tables 2A and 2B show that the combination of Acticide BAC50M (Benzalkonium chloride: referred to as B in tables 2A and 2B), Acticide DDQ 50 (Didecyl Dimethyl Ammonium Chloride: referred to as A (i.e. individual component A rather than composition A above) in tables 2A and 2B), Acticide PHB 20 (Poly Hexamethylene Biguanide Hydrochloride: referred to as E is tables 2A and 2B), Acticide L (Bronopol: referred to as C in tables 2A and 2B) and Acticide PCMC (P-chloro-m-cresol: referred to as D in tables 2A and 2B) provides a greater log reduction against *Pseudomonas aeruginosa* (NCTC 13359) than any one component on its own and any possible combination of three or four of the components. As shown in Table 2B, higher dilutions also provide a disinfecting effect. Without wishing to be bound by theory, it is believed that the combination of Acticide BAC50M, Acticide DDQ 50, Acticide PHB 20, Acticide L and Acticide PCMC, according to compositions of the present invention, provides a synergistic effect in providing a disinfecting action.

Sanitising Water Tests

Dr Susanna Sherwin and Professor Bill Keevil, under a non-disclosure agreement, at the Environmental Healthcare Unit at the University of Southampton, UK, carried out tests on the efficiency of composition A as a water treatment. Their methods and results are set out below, with reference to the figures.

1. Inactivation of *Cryptosporidium parvum*

The tests aimed to determine the concentration of biocide SQ53 (neat composition A) needed to inactivate *Cryptosporidium parvum* oocysts. This was evaluated using Live/Dead staining, which detects whether the membrane of the oocyst has been damaged enough for the 'dead' stain to enter the cell.

A range of dilutions of the neat SQ53 biocide were used. They are detailed in Table 3 below, along with the parts per million of active ingredients for each dilution. Concentrations known as 1:19 v/v and 1:15 v/v are named in this water treatment evaluation as dilutions 5% and 6.25%, respectively.

TABLE 3

Concentrations of biocide SQ53 used in the study, along with their equivalent ppm levels.

| Dilutions of concentrated SQ53 used in studies (%) | Actual parts per million (ppm) of dilutions |
|---|---|
| 10.00 | 16,140.00 |
| 6.25 | 10,087.50 |
| 5.00 | 8,070.00 |
| 2.00 | 3,228.00 |
| 1.00 | 1,614.00 |
| 0.50 | 807.00 |
| 0.20 | 322.80 |
| 0.10 | 161.40 |

A. Incubation of *C. parvum* with Biocide and Subsequent Live/Dead Staining of Oocysts

*Cryptosporidium parvum* oocysts were received in a 1 ml sample with a total of $1 \times 10^7$ oocysts. Each replicate used in this study consisted of a 10 µl aliquot of this stock, containing an average of $1 \times 10^5$ oocysts. Each concentration of biocide examined had three replicates per time-point examined.

Each aliquot of oocysts were incubated for 24 hours in a final volume of 100 µl containing one of a range of concentrations of biocide SQ53 (Table 3). At 1 h prior to the time-point, the controls were subjected to 1 ml acidified HBSS (Hanks balanced salts solution (pH 2.75)) in order to allow the DAPI stain to penetrate the cell membrane. Incubations with the biocide occurred at 37° C., in the dark.

At each time point, the samples were centrifuged at 13,000 rpm in a micro-centrifuge for 95 seconds, the supernatant (containing the biocide) was carefully removed, and the pellet was re-suspended (by vortexing) in neutral HBSS (pH 7) and washed by repeating this process three times. After the final centrifugation step, 100 µl HBSS supernatant was left with the pelleted oocysts, and 10 µl DAPI and 10 µl PI were added to the samples. The oocysts were re-suspended by vortexing, and were incubated with the Live/Dead stains for 2 h at 37° C. in the dark.

After incubation with the live/dead stains, the oocysts were once again washed 2 times by centrifugation and re-suspension in neutral HBSS. After the final centrifugation step, 10-20 µl of supernatant was left with the sample, the oocysts were re-suspended by vortexing, and the total volume was placed in a glass spot slide and allowed to dry. Once the sample was dry, immersion oil was used to place a coverslip, and microscopy of the slides was carried out within 48 hours of sample preparation.

B. Microscopy and analysis of *C. parvum* oocysts

The *C. parvum* oocysts were analysed for the presence of the 'dead' stain PI and the counterstain DAPI. Each sample was examined under oil immersion epifluorescence microscopy, and photographs were taken of as many oocysts as possible, to allow for a count of >100 oocysts per replicate where possible. If oocysts numbers were low, photographs were taken of all oocysts visualised. Numbers of dead and live cells were then counted, and the percentage of live oocysts was calculated for each replicate sample. The average percentage survival was then calculated across the replicates.

Figure 4:
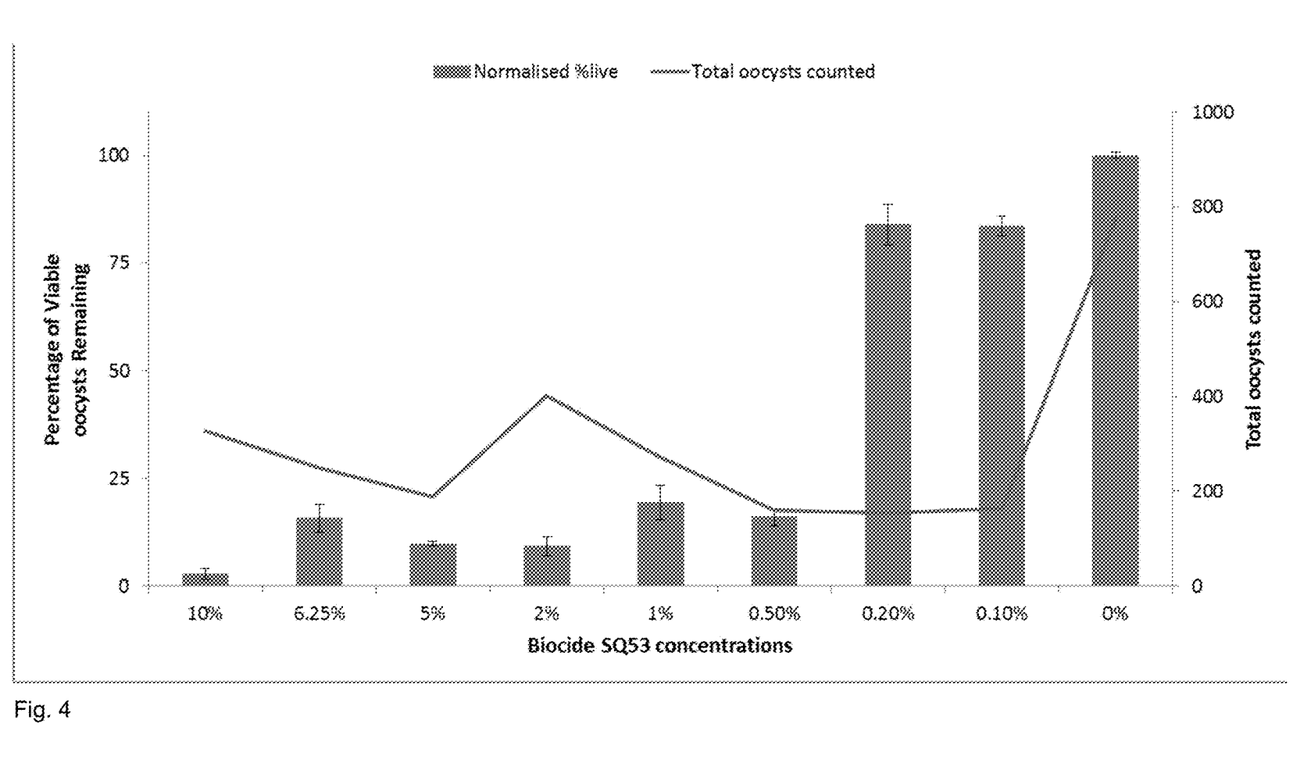
FIG. 4: Shows the percentage survival of *C. parvum* oocysts after 24 h incubation with a range of concentrations of biocide SQ53 (grey bars).

FIG. 4 shows the percentage survival of *C. parvum* oocysts after 24 h incubation with a range of concentrations of biocide SQ53 (grey bars). The total oocysts counted to generate the percentage survival for each bar are shown by the dark grey line. Standard error bars are shown.

C. 24 h Incubation with Biocide

The levels of 'live' *C. parvum* recovered from the samples after incubation with biocide SQ53 for 24 h are shown in FIG. 4. The lowest concentrations of biocide (0.01-0.02% SQ53) showed a maximum of only 16% reduction of viable oocysts after 24 hours, whereas the concentrations of biocide that were 0.5% of the concentrate and over showed a 80-90% reduction of viable oocysts, with the highest biocide concentration showing a 97% reduction of viable oocysts. The levels of oocyst recovery were high in this study and showed no correlation to the level of oocysts survival in the samples, which means that the results can be treated with high confidence.

As mentioned above, contamination of swimming pool and recreational waters with the organism *C. parvum* is a serious problem around the world, for example in the UK. Once the waters become contaminated, it is easy for the organism to be transmitted into humans and infection can occur from as little as 132 oocysts (DuPont et al., (1995), The Infectivity of *Cryptosporidium parvum* in Healthy Volunteers, 332(13): 855-859). The current treatment of these waters with chlorine is ineffective to eliminate this organism, as previous studies have shown that treatment with 4 ppm chlorine at pH 7 for 25 hours resulted in no decrease in cell viability as seen by the DAPI/PI assay, and only a 40% reduction in cell viability when using the excystation assay (Widmer, (2002), Molecular mechanisms of chemical inactivation of *Cryptosporidium* oocysts and *Giardia* cysts, AWWA Research Foundation).

In contrast to this, these tests show that the biocide SQ53 (neat composition A) can result in an 80-90% reduction in cell viability, when concentrations of 0.5% and higher are used. If concentrations of 10% are used, a reduction of 97% can be seen (FIG. 4). This is a far more efficient treatment than 4 ppm chlorine.

2. Inactivation of *Klebsiella pneumoniae*

Dr Susanna Sherwin and Professor Bill Keevil, under a non-disclosure agreement, at the Environmental Healthcare Unit at the University of Southampton, UK, also tested the action of SQ53 (composition A) against the highly antibiotic resistant bacteria *Klebsiella pneumoniae* NDM-1 (New Delhi metallo-β-lactamase). The same concentrations as shown in Table 3, above, were used.

*Klebsiella pneumoniae* was grown at 22° C. overnight in LB broth, with 150 rpm orbital shaking, to an optical density ($OD_{620}$) of 0.6. Biocide SQ53 (composition A) was diluted in sterile water, and working stocks were calculated so that 20 µl of each working stock could be added to 180 µl culture to create final the concentrations shown in Table 3, above. Each control well received 20 µl sterile water in the place of biocide. Upon addition of culture, the plate was incubated at room temperature for 4 hours, and samples were taken for plating at 0 hours, 2 hours, and 4 hours. Samples were neutralised with neutralising broth, diluted in LB, and plated on LB agar plates. Plates were incubated at 37° C. overnight prior to counting viable cells (CFU).

At 2 hours exposure to biocide, a 1/100 dilution of the treated culture was incubated in the dark with 50 µl live/dead stain for 30 minutes. 100 µl of this sample was filtered onto a 0.2 µm pore size black polycarbonate filter and cell counts of total live and dead cells were recorded with episcopic differential interference contrast/epifluorescence (EDIC/EF) microscopy. Each filter was imaged at 10 random fields of view, and averages of these were used to calculate total cell counts per ml of filtered sample.

Calculation of Numbers of Fields of View Per Filter:
One Field of View=11623.58 µm²
Filter membrane diameter=21000.00 µm
Filter membrane area ($\pi r^2$)=346360590.10 µm²
Numbers of Fields of View per filter=346360590.10/11623.58
=29798.099 fields of view Therefore the overall average total cell count per field of view was multiplied by this factor to obtain total cell count per filter, and thus we could calculate total cell count per 1 ml of original culture.

Figure 5:
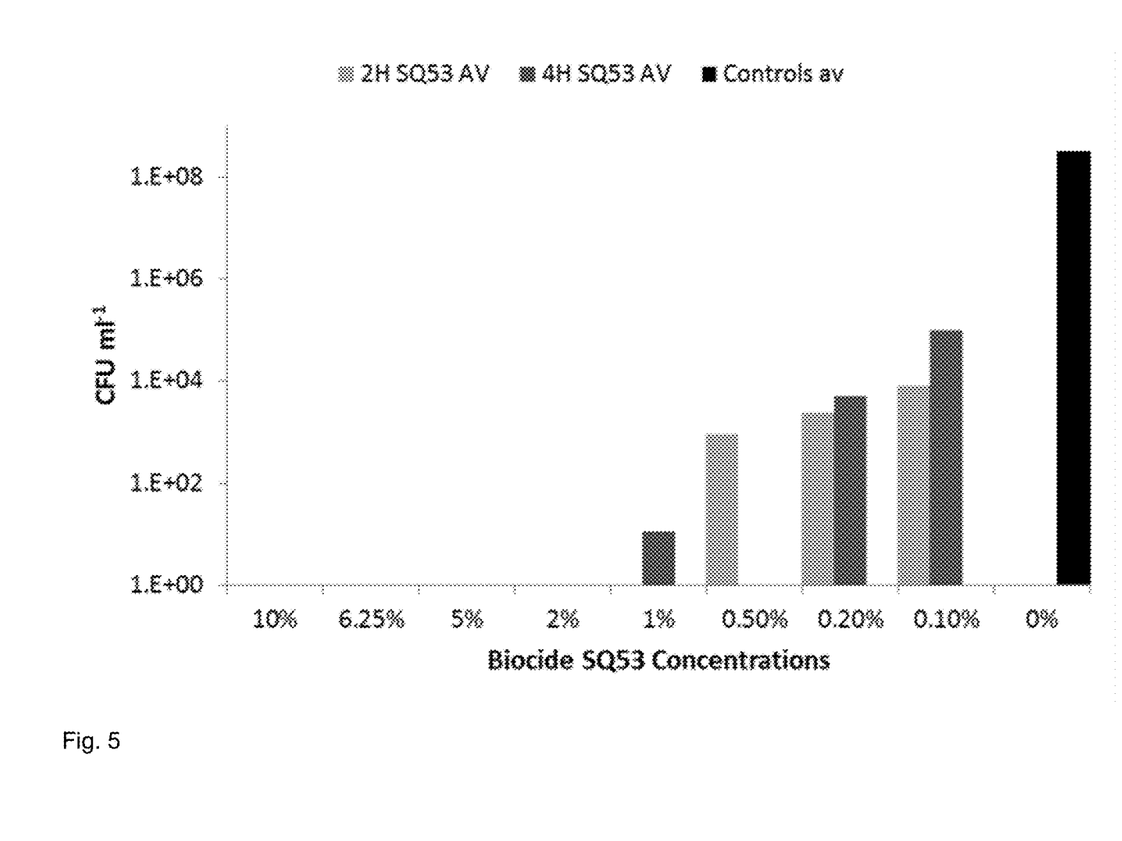
FIG. 5: Bacterial culturability of *K. pneumoniae* after treatment with various concentrations of biocide SQ53.

Treating the bacterium *K. pneumoniae* with SQ53 concentrations of 2% or higher resulted in an 8-log reduction of colony forming units (CFUs), with no culturable bacteria being detected at both 2 and 4 hours (FIG. 5 and Table 4). When lower concentrations of biocide SQ53 were used however, the culturability of the bacteria were more variable, with between 4- to 5-log and 3- to 7-log reductions of bacteria (at 2 h and 4 h respectively), which were proportional to the concentration of biocide tested.

FIG. 5: Bacterial culturability of *K. pneumoniae* after treatment with various concentrations of biocide SQ53. *K. pneumoniae* was treated with SQ53 for 2 and 4 hours. Each study examined the effectiveness of biocide concentrations between 0.1-10%. Colony forming units (CFU·ml$^{-1}$) were calculated after overnight growth at 37° C.

TABLE 4

Log reductions in *Klebsiella pneumoniae* after incubation with 0.1-10% biocide SQ53.

| Biocide concentration (%) | 2H Agar plate assay | 4H Agar plate assay |
|---|---|---|
| 10.00 | 3.08E+08 | 3.08E+08 |
| 6.25 | 3.08E+08 | 3.08E+08 |
| 5.00 | 3.08E+08 | 3.08E+08 |
| 2.00 | 3.08E+08 | 3.08E+08 |
| 1.00 | 3.08E+08 | 2.80E+07 |
| 0.50 | 3.51E+05 | 3.08E+08 |
| 0.20 | 1.29E+05 | 6.14E+04 |
| 0.10 | 3.84E+04 | 3.08E+03 |
| 0.00 | 1.00E+00 | 1.00E+00 |

For the bacterium *K. pneumoniae*, standard culturability tests demonstrated that incubation with the biocide SQ53 resulted in a 4- to 5-log reduction of the bacteria at biocide concentrations of 1% or lower at 2 hours, and a 3- to 7-log reduction of the bacteria at biocide concentrations of 1% or lower at 4 hours. At biocide concentrations of 2% and over, an 8-log reduction of bacteria was seen, with no culturable cells being detected (FIG. 5 and Table 4). This means that at concentrations of 2% and higher, the biocide SQ53 inactivates 8-log of *K. pneumoniae* organisms.

3. Desirable Characteristics of a Water Treatment

Table 5 discusses, qualitatively, desirable properties of water treatment biocides. Table 5 is a modified extract from the book "Directory of Microbicides for the Protection of Materials", edited by Wilfried Paulus, Kluwer Academic Publishers, 2004, Section 5.3, Unhoch et al., "Recreational Water Treatment Biocides". This extract states that the "required characteristics" in the left hand column of Table 5 are desired characteristics of water treatment biocides, for example for use in sanitising recreational water systems.

Table 5 shows that composition A (referred to as SQ53 in Table 5) satisfies the desired characteristics of a water sanitising biocide. Use of composition A in water sanitising provides a combination of characteristics which is not seen in other water sanitising techniques.

| Required Characteristic | Copper Salts | Colloidal Silver | Chlorine | Bromine | Polyhexamethylene biguanide | Ozone | UV | SQ 53 |
|---|---|---|---|---|---|---|---|---|
| Effective against both pathogens and nuisance microor. anisms | Partial | Partial | Yes | Yes | Partial | Yes | Yes | Yes |

| Required Characteristic | Copper Salts | Colloidal Silver | Chlorine | Bromine | Polyhexamethylene biquanide | Ozone | UV | SQ 53 |
|---|---|---|---|---|---|---|---|---|
| Low order of toxicity or preferably non toxic to humans, animals and plant life | Partial | Partial | Yes | Partial | Yes | If controlled | Yes | Yes |
| Safe to handle | Yes | Yes | No | No | Yes | Yes | Yes | Yes |
| Does not degrade into or react with other pool or spa chemicals to form harmful disinfection by roducts | Yes | Yes | No | No | Yes | Yes | Yes | Yes |
| Suitable shelf life at storage temperatures for a minimum of 1 year | Yes | Yes | No | No | Yes | N/A | N/A | Yes |
| Efficacious in presence of and stable to organic impurities from bathers and environment, high and low water temperature, pH variations differing water qualities and sunlight | No | No | No | No | Yes | Yes | No | Yes |
| Should not impart colour, odour or taste to the water | Yes | Yes | No | No | Yes | No | Yes | Yes |
| Able to be monitored with a simple point of use test kit | Yes | Yes | Yes | Yes | No | Yes | No | Yes |
| Should not discolour/damage pool and spa surfaces and equipment | No | No | No | No | Yes | No | Yes | Yes |
| Flocculation performance | No | No | No | No | No | No | No | Yes |
| Biofilm | No | No | Partial | Partial | Partial | Partial | No | Yes |

Stability

Composition A has been found to be stable, i.e. not to lose any of its activity in cleaning surfaces, up to 12 months after initial preparation of the composition.

As can be seen from the above results, it is clear that a product in accordance with the present invention is able to act as a cleaning liquid which has beneficial properties.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A cleaning liquid for inhibiting pathogens, wherein the cleaning liquid comprises, in weight %:

0.5-10 benzalkonium chloride,
0.5-10 didecyl dimethyl ammonium chloride,
0.5-10 poly hexamethylene biguanide hydrochloride,
0.3-5 bronopol, and
0.01-0.1 p-chloro-m-cresol.

2. A cleaning liquid for inhibiting pathogens, wherein the cleaning liquid comprises in weight %:

0.5-10 benzalkonium chloride;
0.5-10 didecyl dimethyl ammonium chloride;
0.5-10 poly hexamethylene biguanide hydrochloride;
0.3-5 bronopol;
0.01-0.1 p-chloro-m-cresol;
3-10 ethanol; and,
0.5-2.5 ethylene glycol;
and/or any intermediate value of each range for each component; the balance being water.

3. A cleaning liquid for inhibiting pathogens, wherein the cleaning liquid comprises in weight %:

3 benzalkonium chloride;
3 didecyl dimethyl ammonium chloride;
3.3 poly hexamethylene biguanide hydrochloride;
0.9 bronopol;

0.04 p-chloro-m-cresol;
4.9 ethanol; and,
1.0 ethylene glycol;
the balance being water.

* * * * *